United States Patent [19]

Wierzbicki et al.

[11] Patent Number: 4,608,384

[45] Date of Patent: Aug. 26, 1986

[54] THIENO[2,3-B] PYRROLE COMPOUNDS AND ANALGESIC USE THEREOF

[75] Inventors: Michel Wierzbicki, Puteaux; Jacques Buré, Neuilly sur Seine, both of France

[73] Assignee: Adir, S.A.R.L., Neuilly-sur-Seine, France

[21] Appl. No.: 560,419

[22] Filed: Dec. 12, 1983

[30] Foreign Application Priority Data

Dec. 16, 1982 [FR] France ........................ 82 21090

[51] Int. Cl.$^4$ ................... C07D 495/04; A61K 31/38
[52] U.S. Cl. ................................. 514/413; 548/453
[58] Field of Search ................... 548/453; 514/413

[56] References Cited

PUBLICATIONS

Burger's Medicinal Chemistry, Fourth Edition, Part III, pp. 703–704 and 1217–1218.
Br. J. Pharmacol. (1973), 49, pp. 86–97.
J. Pharmacol. Exp. Therap. (1964), 80, pp. 300–307.
J. Pharmacol. Exp. Therap. (1964), 125, pp. 237–240.
Evaluation of Drug Activity: Pharmacometrics, Editors: D. R. Laurence–A. L. Bacharach (Academic Press) (1964), vol. 1, pp. 183–203.
La Belle, A. and Tislow, R., J. Pharmacol. Exp. Ther. (1950), 98, 19.
L. F. Sancilio, J. Pharmacol. Exp. Ther. (1969), 168, 199–204.
Winter, C. A., Riseley, E. A., and Nuss, G. W., J. Pharmacol. Exp. Ther. (1963), 141, 369–376.
Chen, I. Y. P. and Beekman, H., Science (1951), 113, 631.
Flower, R. J., Chung, H. S. and Cushman, D. W., Prostaglandins (1973), (4), 325–337.

Primary Examiner—Glennon H. Hollrah
Assistant Examiner—D. B. Springer
Attorney, Agent, or Firm—Gordon W. Hueschen

[57] ABSTRACT

New thieno[2,3-b] pyrrole compounds of the formula:

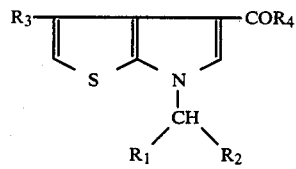

in which:

$R_1$ is hydrogen or lower alkyl, $R_2$ is cyano, carboxy, COOM in which M is alkali alkaline-earth metal, ammonium mono-, di-, or tri-, ($C_1$–$C_5$) alkylammonium optionally substituted by hydroxy, COOR in which R is lower alkyl, or

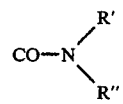

in which R' and R" are hydrogen or lower alkyl;

$R_3$ is lower alkyl; and $R_4$ is lower alkyl, phenyl, halophenyl, lower alkylphenyl, lower alkoxy-phenyl nitrophenyl and di-lower-alkylamino, and enatiomers thereof.

These new compounds may be used as medicines especially in the treatment of acute and chronic pains.

13 Claims, No Drawings

THIENO[2,3-B] PYRROLE COMPOUNDS AND ANALGESIC USE THEREOF

The present invention provides thieno[2,3-b]pyrrole compounds of the formula:

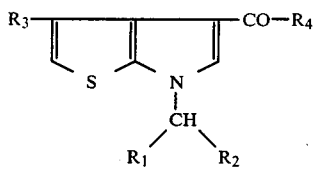
(I)

in which:

$R_1$ is selected from the group consisting of a hydrogen atom and straight- and branched-chain alkyl radicals having from 1 to 5 carbon atoms inclusive;

$R_2$ is selected from the group consisting of
- a cyano radical,
- a carboxy radical,
- a COOM group in which M is selected from the group consisting of alkali and alkaline earth metals, an ammonium radical and mono-, di-, and tri- ($C_1$–$C_5$) alkylammonium radicals, optionally mono- and poly- substituted by a hydroxy radical,
- a COOR group in which R is selected from the group consisting of alkyl radicals having from 1 to 5 carbon atoms inclusive; and
- a

group in which R' and R" which are the same or different are each selected from the group consisting of a hydrogen atom and straight and branched chain alkyl radicals having from 1 to 5 carbon atoms inclusive;

$R_3$ is selected from the group consisting of straight- and branched-chain alkyl radicals having from 1 to 5 carbon atoms inclusive; and $R_4$ is selected from the group consisting of straight and branched chain alkyl radicals having from 1 to 5 carbon atoms, an unsubstitued phenyl radical, and halophenyl, ($C_1$–$C_5$) alkyl phenyl, ($C_1$–$C_5$) alkoxyphenyl, nitrophenyl, and straight- and branched-chain di-($C_1$–$C_5$) alkylamino radicals.

The compounds of the general formula I contain an asymmetric carbon atom. Thus there are two enantiomers corresponding to each of them and these enantiomers are also included in the present invention.

The present invention also relates to a process for the preparation of compounds of the general formula I, characterised in that:

the diazo compounds of the general formula II:

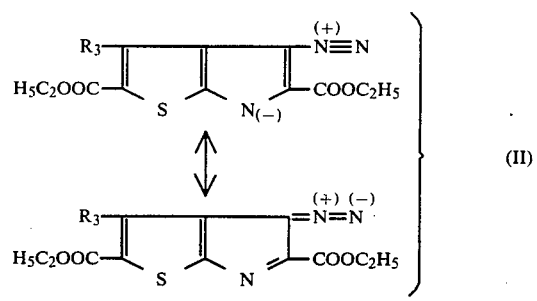
(II)

in which $R_3$ has the meaning defined hereinbefore, are de-diazotised to obtain the compound of the general formula III:

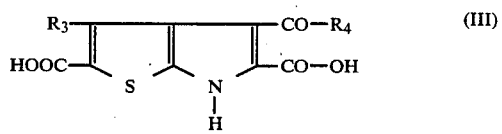
(III)

in which $R_3$ has the meaning given hereinbefore, the compound III so-obtained is acylated according to the Friedel-Craft method by means of an acyl halide of the formula X—CO—$R_4$ in which X represents a halogen atom, especially a bromine or chlorine atom, and $R_4$ has the meaning given hereinbefore, to obtain the compound of the general formula IV:

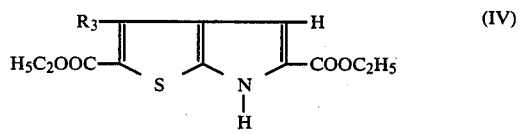
(IV)

in which $R_3$ and $R_4$ have the meanings given hereinbefore, the derivatives IV are hydrolysed to obtain the compounds of the general formula V:

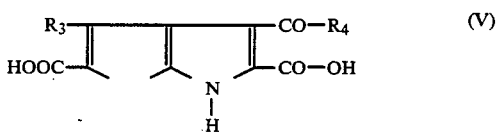
(V)

in which $R_3$ and $R_4$ have the meanings given hereinbefore, these compounds V are decarboxylated to obtain compounds of the general formula VI:

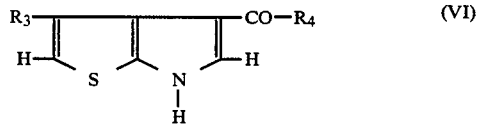
(VI)

in which $R_3$ and $R_4$ have the meanings given hereinbefore, which compounds VI are then N-alkylated by means of an α-halo acid or derivative of the formula:

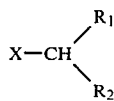

in which $R_1$ and $R_2$ have the meanings given hereinbefore and X represents a halogen atom, such as chlorine or bromine.

It is especially advantageous to effect the dediazotisation of the derivative II either by heating in a suitable solvent, such as, for example, ethanol, if necessary with catalysis of the reaction by traces of HCl, U.V. or radical initiators, or by reduction by means of reducing agents such as, for example, $LiAlH_4$, $NaBH_4$ etc. In the same way, it is especially appropriate for the acylation fo the compounds III to be carried out in the presence of a catalyst (Lewis acid) in an appropriate solvent such as dichloromethane.

The hydrolysis of the compounds IV is expediently carried out by heating the said compounds IV in a base-ethanol mixture, followed by acidification. Finally, the decarboxylation of the compounds V is advantageously carried out by heating in a suitable solvent such as, for example, quinoline, in the presence of copper powder as catalyst.

The starting materials of the general formula II may be prepared according to the method described by Wierzbicki M. et al., Bull. Soc. Chim. France (1975) p. 1786–1792, from compounds of the general formula:

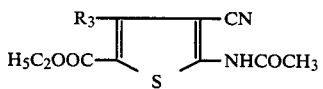

in which $R_3$ has the meaning given hereinbefore.

These latter compounds may themselves be prepared according to the method described by Gewald K. et al., Chem. Ber. (1966), 99, p. 94 and 2712, from starting materials of the general formula:

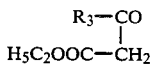

in which $R_3$ has the meaning given hereinbefore, which starting materials, treated with $CN-CH_2-CN$, sulphur, a secondary amine and ethanol, are cyclised forming compounds of the general formula:

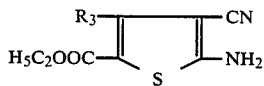

in which $R_3$ is as defined hereinbefore, and these compounds are then N-acetylated by $CH_3COCl/CH_3COOH$.

The compounds of the general formula I have interesting pharmacological properties, in particular chiefly analgesic properties and, to a lesser degree, anti-inflammatory properties.

Their toxicity is low; their $LD_{50}$, determined orally in mice, is between 250 and 2000 mg/kg.

So, for the products of examples 7 and 9 hereinafter, the $LD_{50}$ orally in mice, are respectively of 480 and 680 mg/kg, while under the same conditions, they are respectively of 1150 and 1400 mg/kg for glafenine and clometacine, well known analgesic agents, taken as products of reference.

The analgesic activity of the compounds of the invention has been demonstrated in particular by the test of Hendershot, L. C., Forsaith, J. J., J. Pharmacol. Exp. Ther. (1959), 125, 237, relating to abdominal cramps induced by phenylbenzoquinone, and by the test of Koster R., Anderson M., de Beer E. S., Fed. Proc. (1959), 18, 412, relating to writhing induced by acetic acid. For each of these tests, the average effective dose $ED_{50}$ for the compounds of the invention lies between 5 and 100 mg/kg in the case of oral administration to the Swiss mouse.

For your guidance, it has been noted that, according to the test of hendershot, previously mentioned, the average effective doses $ED_{50}$, one hour after the treatment, for the compounds of examples 7 and 9 hereinafter, were 21.6 and 26.7 mg/kg respectively while it was 43 mg/kg for glafenine. Moreover, for the compounds of the invention the duration of the analgesic effect is much greatest than that observed with the analgesic agents of reference. Thus, with the phenylbenzoquinone test according to Hendershot et al, it was observed in mice that the treatment orally at a dose of 25 mg/kg with the compound of example 7 hereinafter, gives a level of protection which reaches 60% and is maintained for 5 hours, while, under the same conditions with clometacine the level of protection is only 46% and this activity disappears after 3 hours.

The anti-inflammatory activity of the compounds according to the invention has been studied by various tests.

In particular, according to the test of La Belle A. and Tislow R., J. Pharmacol. Exp. Ther. (1950), 98, 19, relating to the pain caused by arthritis induced by silver nitrate, the average effective dose ($ED_{50}$) of the products of the invention lies between 50 and 200 mg/kg in the case of oral administration to a rat.

In the case of the L. F. Sancilio test, J. Pharmacol. Exp. Ther. (1969), 168, 199, relating to pleurisy induced by carrageenin, the products of the invention exhibit very significant activity between 12.5 and 200 mg/kg when administered orally to the Swiss mouse.

Also, according to the test of Winter C. A., Riseley E. A., and Nuss. G. W., J. Pharmacol. Exp. Ther. (1963), 141, 369, relating to granuloma induced by cotton, none of the products of the invention has significant activity at doses lower than 50 mg/kg when administered orally to S.D. rats.

Furthermore, in the hot plate test according to the method described by Chen I. Y. P. and Beekman H., Science (1951), 113, 631, the active doses of the compounds of the invention are higher than 50 mg/kg in the case of subcutaneous administration to NMRI mice, which shows the absence of central activity for the compounds tested in this way.

The application of the test described by Flower R. J., Chung H. S. and Cushman D. W., Prostaglandines (1973), (4), 325, to the compounds of the invention has shown that certain of these compounds are inhibitors of enzymatic systems for prostaglandin synthesis at average inhibitory doses ($ID_{50}$) capable of going down to $10^{-6}M$, which tends to prove that the said products have a mode of action considered to be peripheral.

The pharmacological properties described above as well as the low toxicity of the compounds of the general formula I permits their therapeutic use chiefly in the treatment of acute or chronic pain and especially of pain associated with an inflammatory process (rheumatic pain in arthrosis, arthritis, lumbosciatica, etc . . . ), traumatic, post-traumatic or post-operative pin, pain in the ORL, stomalogical or genito-urinary fields and, equally, certain neuralgia, headaches, migraines and cancer pains.

The present invention relates also to pharmaceutical preparations containing as active ingredient a compound of the general formula I, mixed or in combination with a suitable pharmaceutical excipient like, for example, distilled water, glucose, lactose, starch, talc, ethyl cellulose, magnesium stearate or coconut oil.

The pharmaceutical preparations so obtained are generally in dosage form and can contain from 25 to 250 mg of active ingredient. They may assume, for example, the form of tablets, dragées, gelatin-coated pills, suppositories, injectable or drinkable solutions, or ointments and, depending on the case in question, may be administered orally, rectally, parenterally or locally at a dosage of from 25 to 250 mg from 1 to 4 times per day.

The following Examples illustrate the invention, the melting points, unless indicated to the contrary, being determined by Kofler hot plate.

EXAMPLE 1

2,5-Diethoxycarbonyl-3-methylthieno[2,3-b]pyrrole 1 mole of 2-acetamido-3-cyano-5-ethoxycarbonyl-4-methylthiophene (prepared according to the method described by Gewald K. et al., Chem. Ber. (1966), 99, p. 94 and 2712, from ethyl acetate) is brought to reflux for 24 hours in 1.6 l of acetone with 187 g of ethyl bromoacetate and 250 g of potassium carbonate. Subsequently, the mixture is precipitated in 6 liters of an ice-water mixture (1:1). The whole is vigorously stirred, the resulting precipitate is filtered, dried with air, washed with 500 ml of an iced mixture of water and ethanol (60:40), dried again, and finally washed with 700 ml of a mixture of cyclohexane and benzene (6:1). The resulting product (320 g–0.95 mole) is then stirred in 1.2 liters of $H_2SO_4$ at 30% maintained at a temperature of less than 10° C., in a current of nitrogen. 85 g of potassium nitrite in 180 ml of water are progressively added whilst maintaining the temperature. When the addition is complete, stirring is continued for a few minutes, then 7.2 liters of an ice-water mixture are added. The whole is stirred vigorously. The yellow precipitate obtained is briefly suction-filtered and rinsed with water until almost neutral. It is then brought to reflux in 3 liters of ethanol until the evolution of nitrogen is complete. Subsequently, the reaction mixture is concentrated to 1 liter by distillation, 300 ml of water are added and the whole is stirred vigorously. Once crystallisation is complete, the precipitate is filtered and dried. In this manner 205 g (0.73 mole) of 2,5-diethoxycarbonyl 3-methyl-thieno[2,3-b]pyrrole are obtained, m.p.: 139° C. The following was prepared in the same manner:

2.5-diethoxycarbonyl-3-n-propylthieno[2,3-b]pyrrole, m.p.: 137°–138° C.

EXAMPLE 2

2,5-diethoxycarbonyl-3-methyl-4-parachlorobenzoyl-thieno[2,3-b]pyrrole 70 g (0.25 mole) of 2,5-diethoxycarbonyl-3-methyl-thieno[2,3-b]pyrrole are stirred with 65 g of parachlorobenzoyl chloride and 120 g of tin tetrachloride in 1.2. liters of dichloromethane. The whole is then maintained under gentle reflux for 20 hours. The mixture is then hydrolysed with 500 ml of 4N hydrochloric solution and 500 g of crushed ice. The whole is stirred vigorously until hydrolysis is complete. The aqueous phase is decanted and washed three times with 200 ml of dichloromethane each time. The combined organic phases are washed with water, then with a dilute solution of sodium bicarbonate and finally the solvent is evaporated. In this manner, 105 g of crude 2,5-diethoxycarbonyl-3-4-parachlorobenzoyl-thieno[2,3-b]pyrrole are obtained, which is subsequently used without further purification.

The following were obtained in the same manner:

(a) 2,5-diethoxycarbonyl-3-methyl-4-acetylthieno[2,3-b]pyrrole, (b) 2,5-diethoxycarbonyl-3-methyl-4-orthochlorobenzoylthieno[2,3-b]pyrrole, (c) 2,5-diethoxycarbonyl-3-methyl-4-(2,6-dichlorobenzoyl)-thieno[2,3-b]pyrrole, (d) 2,5-diethoxycarbonyl-3-methyl-4-parafluorobenzoylthieno[2,3-b]pyrrole, (e) 2,5-diethoxycarbonyl-3-methyl-4-metachlorobenzoylthieno[2,3-b]pyrrole, (f) 2,5-diethoxycarbonyl-3-methyl-4-benzoylthieno[2,3-b]pyrrole, (g) 2,5-diethoxycarbonyl-3-methyl-4-paramethoxybenzoylthieno[2,3-b]pyrrole, (h) 2,5-diethoxycarbonyl-3-n.propyl-4-parafluorobenzoylthieno[2,3-b]pyrrole, (i) 2,5-diethoxycarbonyl-3-n.propyl-4-orthochlorobenzoylthieno[2,3-b]pyrrole, (j) 2,5-diethoxycarbonyl-3-methyl-4-orthomethylbenzoylthieno[2,3-b]pyrrole, (k) 2,5-diethoxycarbonyl-3-methyl-4-metamethylbenzoylthieno[2,3-b]pyrrole, (l) 2,5-diethoxycarbonyl-3-methyl-4-paramethylbenzoylthieno[2,3-b]pyrrole.

EXAMPLE 3

2,5-dicarboxy-3-methyl-4-parachlorobenzoylthieno[2,3-b]pyrrole 105 g of crude 2,5-diethoxycarbonyl-3-methyl-4-parachlorobenzoylthieno[2,3-b]pyrrole are heated at reflux in a mixture of 1 liter of ethanol and 1 liter of a normal solution of sodium hydroxide until complete saponification. The ethanol is then eliminated by distillation on a water bath. The aqueous solution is filtered and then acidified. The resulting precipitate is collected by filtration, washed with water, and dried with air and then in vacuo. In this manner, 92 g of crude 2,5-dicarboxy-3-methyl-4-parachlorobenzoylthieno[2,3-b]pyrrole are obtained, which is used in subsequent syntheses without further purification. The following were obtained in the same manner:

(a) 2,5-dicarboxy-3-methyl-4-acetylthieno[2,3-b]pyrrole, (b) 2,5-dicarboxy-3-methyl-4-orthochlorobenzoylthieno[2,3-b]pyrrole, (c) 2,5-dicarboxy-3-methyl-4-(2,6-dichlorobenzoyl)-thieno[2,3-b]pyrrole, (d) 2,5-dicarboxy-3-methyl-4-parafluorobenzoylthieno[2,3-b]pyrrole, (e) 2,5-dicarboxy-3-methyl-4-metachlorobenzoylthieno[2,3-b]pyrrole, (f) 2,5-dicarboxy-3-methyl-4-benzoylthieno[2,3-b]pyrrole, (g) 2,5-dicarboxy-3-methyl-4-paramethoxybenzoyl-thieno[2,3-b]pyrrole,
(h) 2,5-dicarboxy-3-n.propyl-4-parafluorobenzoyl-thieno[2,3-b]pyrrole,
(i) 2,5-dicarboxy,3-n.propyl-4-orthochlorobenzoyl-thieno[2,3-b]pyrrole,
(j) 2,5-dicarboxy-3-methyl-4-orthomethylbenzoyl-thieno[2,3-b]pyrrole,
(k) 2,5-dicarboxy-3-methyl-4-metamethylbenzoyl-thieno[2,3-b]pyrrole,
(l) 2,5-dicarboxy-3-methyl-4-paramethylbenzoyl-thieno[2,3-b]pyrrole.

EXAMPLE 4

3-methyl-4-parachlorobenzoylthieno[2,3-b]pyrrole 92 g of 2,5-dicarboxy-3-methyl-4-parachlorobenzoyl-thieno[2,3-b]pyrrole are heated near reflux in 900 ml of quinoline with 300 mg of copper powder until $CO_2$ is evolved. Once evolution is complete, the whole is allowed to return to room temperature and, while cooling, 200 ml of a 4N solution of hydrochloric acid are then added to the mixture. The whole is stirred very vigorously, the fine precipitate obtained is collected by filtration, washed twice with 50 ml of a normal solution of hydrochloric acid each time, and then with water. The combined aqueous solutions are extracted three times with 150 ml of dichloromethane each time.

The dichloromethane solution thus obtained is washed with water and then evaporated to dryness. The resulting residue is taken up in a minimum of dichloromethane and yields a crystallised compound which is added to the earlier one. The whole is recrystallised from aqueous ethanol. In this manner 56.5 g of 3-methyl-4-parachlorobenzoylthieno[2,3-b]pyrrole are obtained, m.p.: 223° C.

The following were obtained in the same manner:
(a) 3-methyl-4-acetylthieno[2,3-b]pyrrole, m.p.: 183° C.,
(b) 3-methyl-4-benzoylthieno[2,3-b]pyrrole, m.p.: 230.5° C.,
(c) 3-methyl-4-(2,6-dichlorobenzoyl)-thieno[2,3-b]pyrrole, m.p.: 219° C.,
(d) 3-n.propyl-4-orthochlorobenzoylthieno[2,3-b]pyrrole, m.p.: 108°–109° C.,
(e) 3-methyl-4-metachlorobenzoylthieno[2,3-b]pyrrole, m.p.: 221°–222° C.,
(f) 3-methyl-4-orthochlorobenzoylthieno[2,3-b]pyrrole, m.p.: 186° C.,
(g) 3-methyl-4-parafluorobenzoylthieno[2,3-b]pyrrole, m.p.: 245° C.,
(h) 3-n.propyl-4-parafluorobenzoylthieno[2,3-b]pyrrole, m.p.: 157° C.,
(i) 3-methyl-4-paramethoxybenzoylthieno[2,3-b]pyrrole, m.p.: 215° C.,
(j) 3-methyl-4-orthomethylbenzoylthieno[2,3-b]pyrrole,
(k) 3-methyl-4-metamethylbenzoylthieno[2,3-b]pyrrole,
(l) 3-methyl-4-paramethylbenzoylthieno[2,3-b]pyrrole.

EXAMPLE 5

3-methyl-4-parachlorobenzoyl-6-(α-carboxyethyl)-thieno[2,3-b]pyrrole 34 g of 3-methyl-4-parachlorobenzoylthieno[2,3-b]pyrrole are added to a solution of sodium ethoxide obtained by dissolving 5.66 g of sodium in 400 ml of ethanol. There are then added dropwise, while stirring, 44 g of ethyl α-bromopropionate in 150 ml of ethanol, and the whole is maintained at reflux for 4 hours. The mixture obtained is hydrolysed, without being purified, by adding 150 ml of a normal sodium hydroxide solution and heating at reflux for several minutes.

The ethanol is then evaporated by distillation. The mixture is diluted by half its volume with water, and the whole is extracted with 500 ml of dichloromethane. The dichloromethane phase is washed twice with 25 ml of normal sodium hydroxide solution each time and the aqueous phase is washed twice with 50 ml of dichloromethane each time. This aqueous phase, acidified to a pH value of <1, is extracted again with dichloromethane. The organic phase, washed with water and then treated with animal charcoal, is subsequently evaporated. The crystallised residue obtained is washed with 200 ml of a mixture of benzene and cyclohexane 1:1. In this manner 36 g of 3-methyl-4-para-chlorobenzoyl-6-(α-carboxyethyl)-thieno[2,3-b]pyrrole are obtained, m.p.: 149° C.

EXAMPLE 6 to 19

The following compounds were prepared in accordance with the process described in Example 5:
(6) 3-methyl-4-parachlorobenzoyl-6-carboxymethyl-thieno[2,3-b]pyrrole, m.p.: 119° C.,
(7) 3-methyl-4-orthochlorobenzoyl-6-(α-carboxyethyl)-thieno[2,3-b]pyrrole, m.p.: 188° C.,
(8) 3-methyl-4-(2,6-dichlorobenzoyl)-6-(α-carboxyethyl)-thieno[2,3-b]pyrrole, m.p.: 186° C.,
(9) 3-methyl-4-benzoyl-6-(α-carboxyethyl)-thieno[2,3-b]pyrrole, m.p.: 152° C.,
(10) 3-n.propyl-4-parafluorobenzoyl-6-carboxymethyl-thieno[2,3-b]pyrrole, m.p.: 199° C.,
(11) 3-methyl-4-orthochlorobenzoyl-6-carboxymethyl-thieno[2,3-b]pyrrole, m.p.: 188° C.,
(12) 3-n.propyl-4-orthochlorobenzoyl-6(α-carboxyethyl)-thieno[2,3-b]pyrrole, m.p.: 158° C.,
(13) 3-methyl-4-acetyl-6-carboxymethylthieno[2,3-b]pyrrole, m.p.: 190° C.,
(14) 3-methyl-4-parafluorobenzoyl-6-(α-carboxyethyl)-thieno[2,3-b]pyrrole,
(15) 3-methyl-4-metachlorobenzoyl-6-(α-carboxyethyl)-thieno[2,3-b]pyrrole,
(16) 3-methyl-4-paramethoxybenzoyl-6-carboxymethyl-thieno[2,3-b]pyrrole,
(17) 3-methyl-4-orthomethylbenzoyl-6-(α-carboxyethyl)-thieno[2,3-b]pyrrole, m.p.: 142° C.,
(18) 3-methyl-4-metamethylbenzoyl-6-(α-carboxyethyl)-thieno[2,3-b]pyrrole, m.p.: 149° C.,
(19) 3-methyl-4-paramethylbenzoyl-6-(α-carboxyethyl)-thieno[2,3-b]pyrrole.

The compounds of examples 14 to 16 are poorly crystallised or oily. The sodium salt of each was prepared by dissolving the acid in a stoichiometric amount of N/10 sodium hydroxide, evaporating the water and drying the residue obtained.

The products obtained in this manner are amorphous and hygroscopic solids, which have been tested in this form.

EXAMPLE 20 to 24

The salts of the acid compounds of the formula I were prepared as follows:

The acid compound, in solution in a suitable solvent such as for example ethanol), methylene chloride or benzene is neutralized with a stoichiometric amount of base such, for example, sodium hydroxide, carbonates and bicarbonates, amines alkylamines and hydroxyalkyl amines. The product obtained by evaporation of the solvent, is recrystallized in a suitable solvent or mixture of solvents such as for example, ethanol, ether, benzene or cyclohexane. According to this method the following compounds were prepared:

(20) sodium salt of 3-methyl-4-benzoyl-6-(α-carboxyethyl)-thieno[2,3-b]pyrrole,
(21) tert.butylamine salt of 3-methyl-4-benzoyl-6-(α-carboxyethyl)-thieno[2,3-b]pyrrole, m.p.: 149° C.,
(22) dimethylaminoethanol salt of 3-methyl-4-benzoyl-6(α-carboxyethyl)-thieno[2,3-b]pyrrole, m.p.: 112° C.
(23) choline salt of 3-methyl-4-benzoyl-6(α-carboxyethyl)-thieno[2,3-b]pyrrole, m.p.: 155° C.
(24) dimethylaminoethanol salt of 3-methyl-4-ortho-chlorobenzoyl-6(α-carboxyethyl)-thieno[2,3-b]pyrrole, m.p.: 101° C.

We claim:

1. A compound selected from the group consisting of: thieno[2,3-b]pyrrole compounds of the formula:

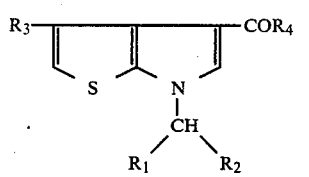

in which
$R_1$ is selected from the group consisting of hydrogen, and straight and branched alkyl having from 1 to 5 carbon atoms inclusive
$R_2$ is selected from the group consisting of:
  carboxy,
  COOM in which M is selected from the group consisting of alkali metals, ammonium, mono-, di-, and tri- ($C_1$–$C_5$) alkylammonium and these radicals mono-substituted by hydroxy;
  COOR in which R is selected from the group consisting of alkyl having from 1 to 5 carbon atoms inclusive
$R_3$ is selected from the group consisting of straight and branched alkyl having from 1 to 5 carbon atoms inclusive
$R_4$ is selected from the group consisting of and alkyl having from 1 to 5 carbon atoms inclusive phenyl, halophenyl, ($C_1$–$C_5$) alkylphenyl and ($C_1$–$C_5$)alkoxyphenyl.

2. A compound of claim 1 selected from the group consisting of thieno[2,3-b]pyrrole compounds of the formula I wherein
  $R_1$ is methyl,
  $R_2$ is carboxy,
  $R_3$ is methyl, and
  $R_4$ is selected from the group consisting of phenyl, ortho-chlorophenyl, and ortho-methylphenyl.

3. A compound of claim 1 which is: 3-methyl-4-parachlorobenzoyl-6-(α-carboxyethyl)-thieno[2,3-b]pyrrole.

4. A compound of claim 1 which is: 3-methyl-4-parachlorobenzoyl-6-carboxymethyl-thieno[2,3-b]pyrrole.

5. A compound of claim 1 which is 3-methyl-4-ortho-chlorobenzoyl-6-(α-carboxyethyl)-thieno[2,3-b]pyrrole.

6. A compound of claim 1 which is 3-methyl-4-(2,6-dichlorobenzoyl)-6-(α-carboxyethyl)-thieno[2,3-b]pyrrole.

7. A compound of claim 1 which is 3-methyl-4-benzoyl-6-(α-carboxyethyl)-thieno[2,3-b]pyrrole.

8. A compound of claim 1 which is: 3-n.propyl-4-parafluorobenzoyl-6-carboxymethyl-thieno[2,3-b]pyrrole.

9. A compound of claim 1 which is: 3-methyl-4-ortho-chlorobenzoyl-6-carboxymethyl-thieno[2,3-b]pyrrole.

10. A compound of claim 1 which is: 3n.propyl-4-ortho-chlorobenzoyl-6-(α-carboxyethyl)-thieno[2,3-b]pyrrole.

11. A compound of claim 1 which is 3-methyl-4-acetyl-6-carboxymethyl-thieno[2,3-b]pyrrole.

12. The pharmaceutical compositions containing as active ingredient an effective analgesic amount of a compound of claim 1, together with a suitable pharmaceutical carrier.

13. A method for treating a living animal body afflicted with pain comprising the step of administering to the said living animal an effective analgesic amount of a compound of claim 1 which is effective for the alleviation of the said condition.

* * * * *

UNITED STATES PATENT AND TRADEMARK OFFICE
CERTIFICATE OF CORRECTION

PATENT NO. : 4,608,384

DATED : August 26, 1986

INVENTOR(S) : Michel Wierzbicki and Jacques Buré

It is certified that error appears in the above-identified patent and that said Letters Patent is hereby corrected as shown below:

Title Page, [56] References Cited, PUBLICATIONS, line 13; "Riseley," should read -- Risley, --

Title Page, [56] References Cited, PUBLICATIONS, line 15; "I. Y. P." should read -- J. Y. P. --

Title Page, [56] References Cited, PUBLICATIONS, line 15; "Beekman," should read -- Beckman, --

Title Page, [56] References Cited, PUBLICATIONS, line 17; "Chung," should read -- Cheung, --

Col. 1, line 55; "unsubstitued" should read -- unsubstituted --

Col. 3, line 17; "fo" should read -- of --

Col. 4, line 8; "E. S.," should read -- E. J., --

Col. 4, line 15; "hendershot" should read -- Hendershot --

Col. 4, line 21; "greatest" should read -- greater --

Col. 4, line 45; "Riseley" should read -- Risley --

Col. 4, line 52; "I. Y. P." should read -- J. Y. P. --

Col. 4, line 52; "Beekman" should read -- Beckman --

Col. 4, line 59; "Chung" should read -- Cheung --

Col. 4, line 59; "Prostaglandines" should read -- Prostaglandins --

Col. 5, line 4; "pin" should read -- pain --

Col. 5, line 55; "manner 205" should read -- manner, 205 --

UNITED STATES PATENT AND TRADEMARK OFFICE
CERTIFICATE OF CORRECTION

PATENT NO. : 4,608,384  Page 2 of 2

DATED : August 26, 1986

INVENTOR(S) : Michel Wierzbicki and Jacques Buré

It is certified that error appears in the above-identified patent and that said Letters Patent is hereby corrected as shown below:

Col. 5, line 59; "2.5-" should read -- 2,5- --
Col. 9, line 39; "inclusive" should read -- inclusive; --

Col. 9, line 43; delete "and"
Col. 9, line 44; inclusive phenyl," should read -- inclusive, phenyl, --

Col. 10, line 1; "alkylphenyl and" should read -- alkylphenyl, and --

Signed and Sealed this

Twenty-fourth Day of March, 1987

*Attest:*

DONALD J. QUIGG

*Attesting Officer*   *Commissioner of Patents and Trademarks*